(12) United States Patent
Anderson

(10) Patent No.: US 12,714,560 B2
(45) Date of Patent: Aug. 25, 2026

(54) BALLOON EXPANDABLE DELIVERY SYSTEM WITH ACTUATED VALVE RETENTION

(71) Applicant: BOSTON SCIENTIFIC SCIMED, INC., Maple Grove, MN (US)

(72) Inventor: James M. Anderson, Corcoran, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 992 days.

(21) Appl. No.: 17/939,253

(22) Filed: Sep. 7, 2022

(65) Prior Publication Data

US 2023/0073466 A1 Mar. 9, 2023

Related U.S. Application Data

(60) Provisional application No. 63/241,613, filed on Sep. 8, 2021.

(51) Int. Cl.
*A61F 2/24* (2006.01)
*A61F 2/95* (2013.01)
*A61M 25/10* (2013.01)

(52) U.S. Cl.
CPC .......... *A61F 2/2433* (2013.01); *A61F 2/9522* (2020.05); *A61M 2025/1084* (2013.01)

(58) Field of Classification Search
CPC .... A61F 2/2433; A61F 2/9522; A61F 2/2436; A61F 2/958; A61F 2230/0091; A61M 2025/1084; A61M 25/10
See application file for complete search history.

(56) References Cited

U.S. PATENT DOCUMENTS

| | | | |
|---|---|---|---|
| 6,280,412 | B1 | 8/2001 | Pederson et al. |
| 7,208,002 | B2 | 4/2007 | Shelso |
| 7,947,070 | B2 | 5/2011 | Headley et al. |
| 10,426,608 | B2 | 10/2019 | Salahieh et al. |

(Continued)

FOREIGN PATENT DOCUMENTS

| | | | |
|---|---|---|---|
| WO | 2013016681 | A2 | 1/2013 |
| WO | 2021163635 | A1 | 8/2021 |

OTHER PUBLICATIONS

International Search Report and Written Opinion dated Dec. 19, 2022 for International Application No. PCT/US2022/042702.

*Primary Examiner* — Thomas C Barrett
*Assistant Examiner* — Mikail A Mannan
(74) *Attorney, Agent, or Firm* — Seager, Tufte & Wickhem LLP

(57) ABSTRACT

A delivery system for an expandable prosthetic heart valve is provided. The delivery system includes an elongate inner member, a distal stop and a proximal stop both disposed on the elongate inner member. At least one of the proximal and distal stops is fixed to the elongate inner member. The delivery system also includes a flexible member disposed around the elongate inner member and having a distal end, a central region, and a proximal end, and an inflatable balloon disposed over the flexible member. The flexible member is configured such that when a heart valve is crimped onto the central region, the central region compresses and proximal and distal regions of the flexible member expand radially to prevent axial movement of the valve.

19 Claims, 10 Drawing Sheets

(56) References Cited

U.S. PATENT DOCUMENTS

| | | | | |
|---|---|---|---|---|
| 2011/0125132 | A1* | 5/2011 | Krolik ............. | A61M 25/10185<br>604/509 |
| 2013/0030519 | A1* | 1/2013 | Tran ........................ | A61F 2/958<br>623/2.11 |
| 2020/0179116 | A1 | 6/2020 | Zhu et al. | |

* cited by examiner 400
423
460
470
435
428
437
490
421
422
430
420
410
440

BALLOON EXPANDABLE DELIVERY SYSTEM WITH ACTUATED VALVE RETENTION

CROSS-REFERENCE TO RELATED APPLICATIONS

This application claims the benefit of priority of U.S. Provisional Application No. 63/241,613 filed Sep. 8, 2021, the entire disclosure of which is hereby incorporated by reference.

TECHNICAL FIELD

The disclosure pertains to medical devices and more particularly to prosthetic heart valve delivery systems, and methods for using such medical devices.

BACKGROUND

Heart valve surgery is used to repair or replace diseased heart valves. A wide variety of endovascular valve replacement procedures and delivery systems have been developed. Some of these systems include valves with self-expanding stent elements. Other systems include balloon expandable stent elements. These devices and systems may be used according to any one of a variety of methods. Of the known medical devices and methods, each has certain advantages and disadvantages. There is an ongoing need to provide alternative medical devices and systems as well as alternative methods for manufacturing and using medical devices.

SUMMARY

This disclosure provides design, material, manufacturing method, and use alternatives for medical devices and systems. An example delivery system for an expandable prosthetic heart valve includes an elongate inner member, a distal stop disposed on the elongate inner member and a proximal stop spaced apart from the distal stop and disposed on the elongate inner member, wherein at least one of the proximal and distal stops is fixed to the elongate inner member, a flexible member disposed around the elongate inner member, the flexible member having a distal end fixed to the distal stop, a central region, and a proximal end fixed to the proximal stop, and an inflatable balloon disposed over the flexible member, wherein the flexible member is configured such that when a heart valve is crimped onto the central region, the central region compresses and proximal and distal regions of the flexible member expand radially to prevent axial movement of the heart valve.

Alternatively or additionally to the embodiment above, the elongate inner member defines a guidewire lumen.

Alternatively or additionally to any of the embodiments above, the flexible member is biased in a relaxed configuration with the central region spaced apart from the elongate inner member.

Alternatively or additionally to any of the embodiments above, when in the relaxed configuration, outer diameters of the central region, proximal region, and distal region are substantially the same.

Alternatively or additionally to any of the embodiments above, the flexible member is a coil.

Alternatively or additionally to any of the embodiments above, the flexible member is a braid.

Alternatively or additionally to any of the embodiments above, the delivery system further comprises a textile woven mesh disposed over the braid.

Alternatively or additionally to any of the embodiments above, the flexible member is a frame including a plurality of struts spaced apart circumferentially around the elongate inner member, each strut having linear regions and bend regions.

Alternatively or additionally to any of the embodiments above, the proximal stop is fixed to the elongate inner member and the distal stop is slidable relative to the elongate inner member, the delivery system further comprising a pull wire fixed to the distal stop and extending proximally therefrom, wherein proximally pulling the pull wire moves the flexible member from a biased relaxed configuration in which the central region is spaced apart from the elongate inner member, to a compressed configuration in which the central region is adjacent the elongate inner member and the distal and proximal regions of the frame are radially expanded.

Alternatively or additionally to any of the embodiments above, the frame includes protrusions on an inner surface of at least some of the plurality of struts, the protrusions configured to slide along the elongate inner member as the central region of the frame compresses and the proximal and distal regions expand.

Alternatively or additionally to any of the embodiments above, the delivery system further comprises a prosthetic heart valve crimped onto the central region, wherein the proximal and distal regions of the flexible member extend radially outward beyond an outer diameter of the crimped heart valve.

Another example delivery system for an expandable prosthetic heart valve includes an elongate inner member defining an inner lumen, a distal stop fixed to the elongate inner member and a proximal stop fixed to the elongate inner member, the proximal stop spaced apart from the distal stop, a flexible member disposed around the elongate inner member, the flexible member having a distal end fixed to the distal stop, a central region, and a proximal end fixed to the proximal stop, the flexible member biased in a relaxed configuration with the central region spaced apart from the elongate inner member, and an inflatable balloon disposed over the flexible member, wherein the flexible member is configured such that when a heart valve is crimped onto the central region, the central region moves from the relaxed configuration to a compressed configuration in which the central region is adjacent the elongate inner member and proximal and distal regions of the flexible member expand radially to prevent axial movement of the heart valve.

Alternatively or additionally to any of the embodiments above, when in the relaxed configuration, outer diameters of the central region, proximal region, and distal region are substantially the same.

Alternatively or additionally to any of the embodiments above, the flexible member is a coil.

Alternatively or additionally to any of the embodiments above, the flexible member is a braid.

Alternatively or additionally to any of the embodiments above, the delivery system further includes a textile woven mesh disposed over the braid.

Alternatively or additionally to any of the embodiments above, the delivery system further includes a prosthetic heart valve crimped onto the central region, wherein the proximal and distal regions of the flexible member extend radially outward beyond an outer diameter of the crimped heart valve.

A further example delivery system for an expandable prosthetic heart valve includes an elongate inner member, a distal stop fixed to the elongate inner member and a proximal stop spaced apart from the distal stop and fixed to the elongate inner member, a flexible member disposed around the elongate inner member, the flexible member having a distal portion fixed to the distal stop, and a separate proximal portion fixed to the proximal stop, wherein the distal portion and the proximal portion are spaced apart longitudinally, wherein a proximal section of the distal portion and a distal section of the proximal portion define a central region configured to receive a heart valve, and an inflatable balloon disposed over the flexible member, wherein the flexible member is configured such that when the heart valve is crimped onto the central region, the proximal portion of the flexible member moves proximally into a radially expanded configuration, and the distal portion of the flexible member moves distally into a radially expanded configuration, thereby preventing axial movement of the heart valve.

Alternatively or additionally to the embodiment above, the distal portion and the proximal portion of the flexible member are frames including a plurality of struts spaced apart circumferentially around the elongate inner member, each strut having linear regions and bend regions.

Alternatively or additionally to any of the embodiments above, the delivery system further includes a plurality of protrusions disposed on an inner surface of at least some of the plurality of struts, wherein the plurality of protrusions are configured to slide along the elongate inner member as the plurality of struts move axially when the distal and proximal portions of the flexible member move into the radially expanded configuration.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

Figure 1:
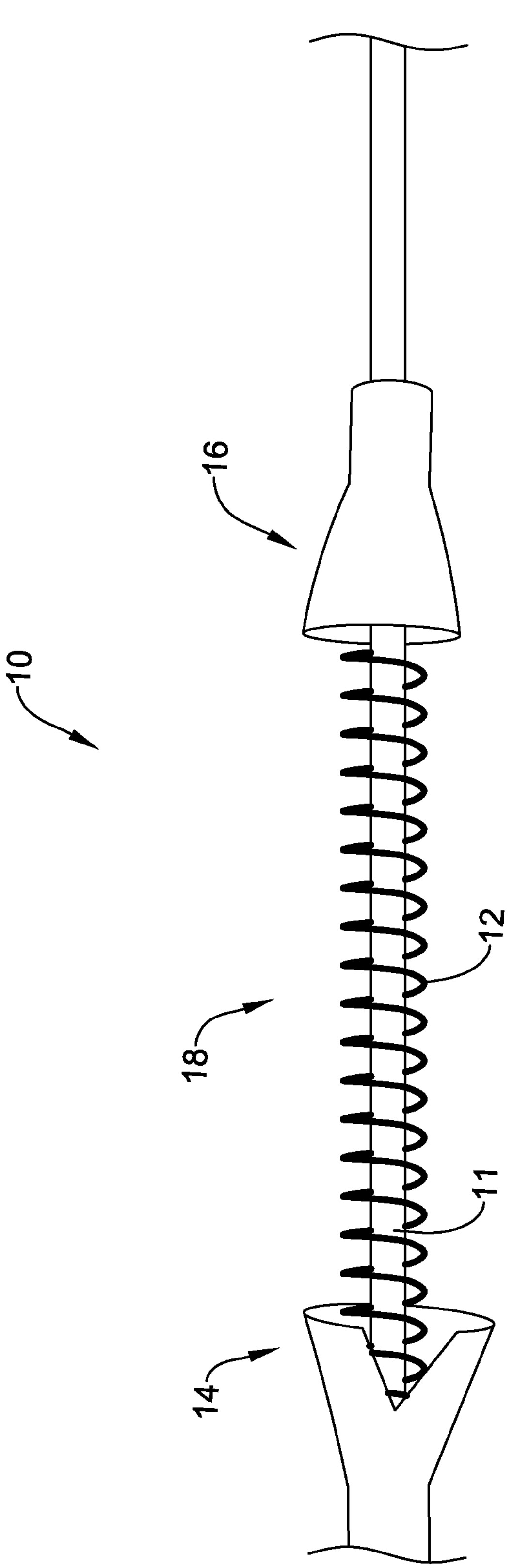
FIG. 1 illustrates a prior art heart valve retention device.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5). Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "withdraw", variants thereof, and the like, may be generally considered with respect to the positioning, direction, and/or operation of various elements relative to a user/operator/manipulator of the device, wherein "proximal" and "withdraw" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a “minimum”, which may be understood to mean a smallest measurement of the stated or identified dimension. For example, “outer extent” may be understood to mean a maximum outer dimension, “radial extent” may be understood to mean a maximum radial dimension, “longitudinal extent” may be understood to mean a maximum longitudinal dimension, etc. Each instance of an “extent” may be different (e.g., axial, longitudinal, lateral, radial, circumferential, etc.) and will be apparent to the skilled person from the context of the individual usage. Generally, an “extent” may be considered a greatest possible dimension measured according to the intended usage, while a “minimum extent” may be considered a smallest possible dimension measured according to the intended usage. In some instances, an “extent” may generally be measured orthogonally within a plane and/or cross-section, but may be, as will be apparent from the particular context, measured differently—such as, but not limited to, angularly, radially, circumferentially (e.g., along an arc), etc.

The terms “monolithic” and “unitary” shall generally refer to an element or elements made from or consisting of a single structure or base unit/element. A monolithic and/or unitary element shall exclude structure and/or features made by assembling or otherwise joining multiple discrete elements together.

It is noted that references in the specification to “an embodiment”, “some embodiments”, “other embodiments”, etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a “first” element may later be referred to as a “second” element, a “third” element, etc. or may be omitted entirely, and/or a different feature may be referred to as the “first” element. The meaning and/or designation in each instance will be apparent to the skilled practitioner.

The following description should be read with reference to the drawings, which are not necessarily to scale, wherein similar elements in different drawings are numbered the same. The detailed description and drawings are intended to illustrate but not limit the disclosure. Those skilled in the art will recognize that the various elements described and/or shown may be arranged in various combinations and configurations without departing from the scope of the disclosure. The detailed description and drawings illustrate example embodiments of the disclosure. However, in the interest of clarity and ease of understanding, while every feature and/or element may not be shown in each drawing, the feature(s) and/or element(s) may be understood to be present regardless, unless otherwise specified.

Some mammalian hearts (e.g., human, etc.) include four heart valves: a tricuspid valve, a pulmonary valve, an aortic valve, and a mitral valve. Some relatively common medical conditions may include or be the result of inefficiency, ineffectiveness, or complete failure of one or more of the valves within the heart. Treatment of defective heart valves poses other challenges in that the treatment often requires the repair or outright replacement of the defective valve. Such therapies may be highly invasive to the patient. Disclosed herein are systems, devices, and/or methods that may be used within a portion of the cardiovascular system in order to diagnose, treat, and/or repair elements such as one or more of the heart valves. At least some of the systems, devices, and/or methods disclosed herein may be used percutaneously and, thus, may be much less invasive to the patient.

Delivering a replacement heart valve endovascularly often requires steering a catheter along complex curves with the valve disposed on a valve holding device. It is desired to maintain the valve stationary on the valve holding device, however steering the device through the complex curves may result in shifting of the valve on the holding device. This may result in misalignment of the valve during deployment.

FIG. 1 illustrates a conventional valve holding device 10 which may be connected to a delivery catheter (not shown). The valve holding structure may include an inner tube 11 with a retention coil 12. A distal stop 14 and a proximal stop 16 may define a valve retaining region 18.

Figure 2:
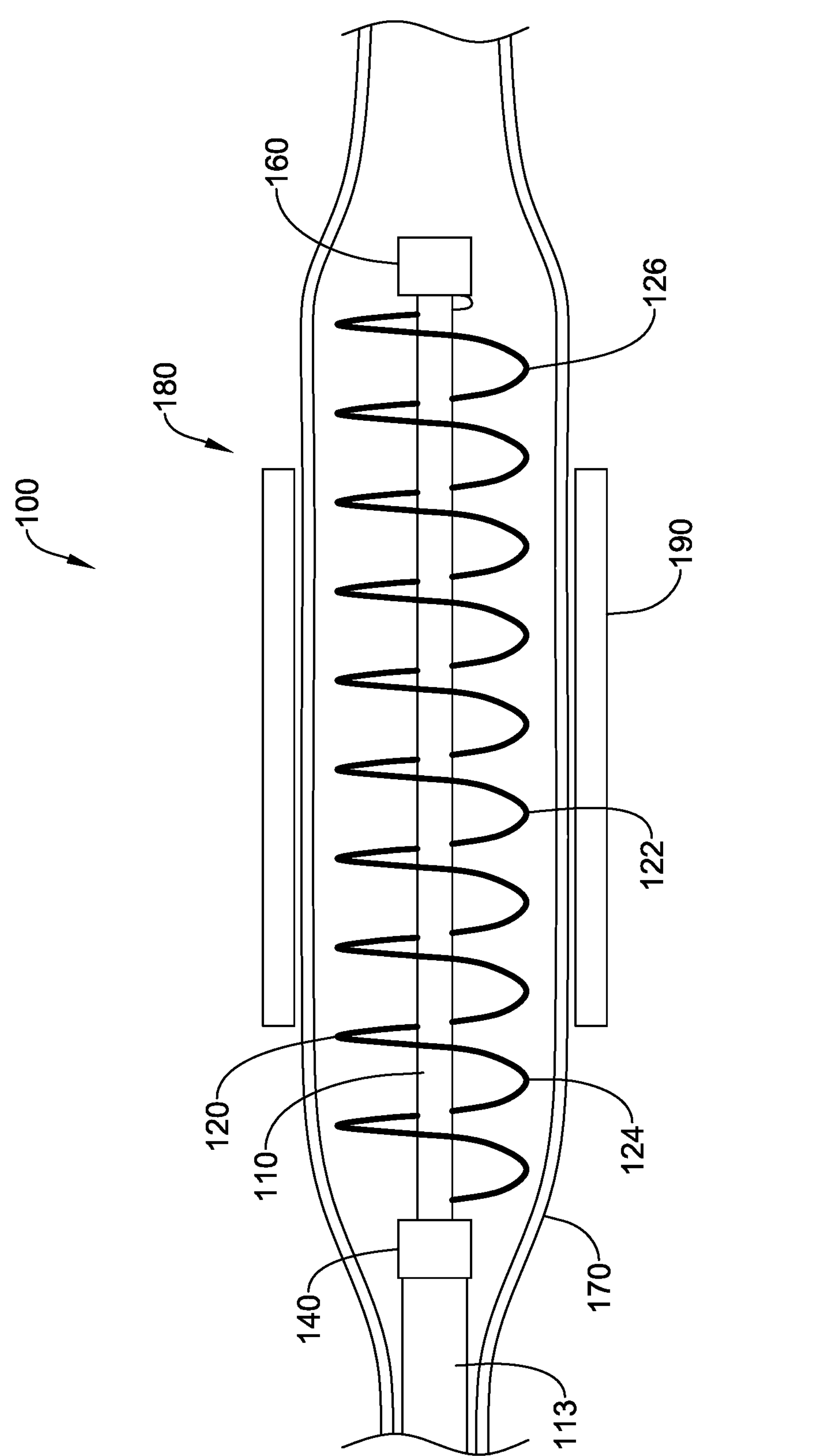
FIG. 2 illustrates an example heart valve delivery system before the valve is crimped onto the central region.

FIG. 2 illustrates an example heart valve delivery system 100 for delivering a balloon expandable prosthetic heart valve 190. The delivery system 100 may include an elongate inner member 110, and a flexible member 120 disposed around the elongate inner member 110. The elongate inner member 110 may define an inner lumen 113, such as a guidewire lumen. The flexible member 120 may be configured to be compressed and then return to a relaxed, expanded configuration. The flexible member 120 may be biased in the relaxed configuration, with the central region 122 of the flexible member 120 spaced apart from the elongate inner member, as shown in FIG. 2. In some embodiments, when in the relaxed configuration, the outer diameters of the central region 122, proximal region 126, and distal region 124 of the flexible member 120 may be substantially the same. In the example shown in FIG. 2, the flexible member 120 is a coil.

The distal end of the flexible member 120 may be fixed to a distal stop 140 which is disposed on the elongate inner member 110. The proximal end of the flexible member 120 may be fixed to a proximal stop 160 which is spaced apart from the distal stop 140 and disposed on the elongate inner member 110. At least one of the distal stop 140 and the proximal stop 160 may be fixed to the elongate inner member 110. In some embodiments, both the distal stop 140 and the proximal stop 160 may be fixed to the elongate inner member 110. In other embodiments, the distal stop 140 may be slidably disposed on the elongate inner member 110. An inflatable balloon 170 may be disposed over the flexible member 120, distal stop 140, and proximal stop 160. The balloon 170 may be fixed to the inner member 110 or other portions of the delivery catheter (not shown) distal of the distal stop 140 and proximal of the proximal stop 160. Inflation fluid may be delivered to the balloon 170 and flow over the inner member 110 and through the flexible member 120.

Figure 3:
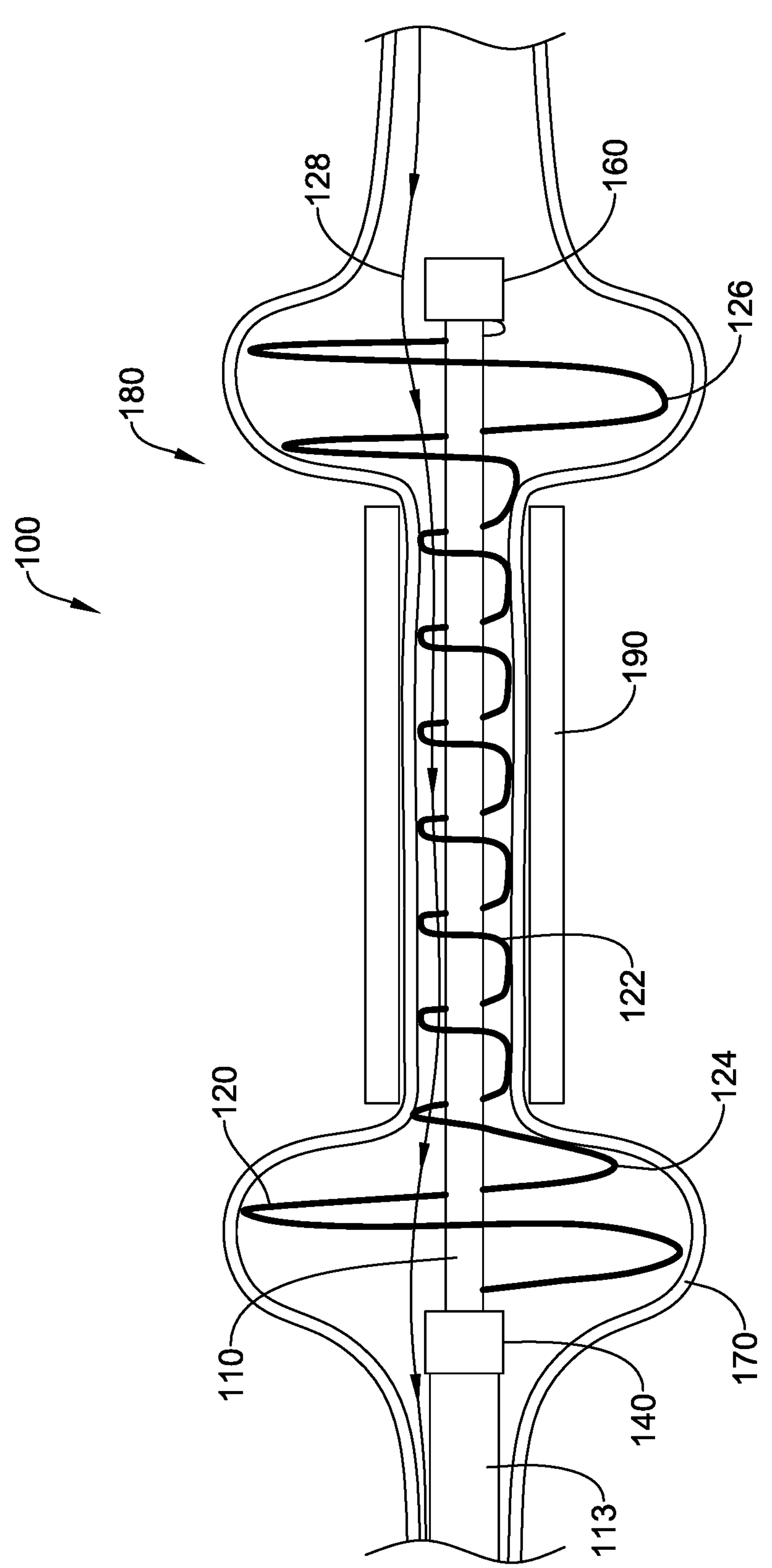
FIG. 3 illustrates the heart valve delivery system of FIG. 2 with the valve crimped onto the central region.

The prosthetic heart valve 190 may be crimped onto the balloon 170 in the valve retaining region 180 over the central region 122 of the flexible member 120. The flexible member 120 may be configured such that when the heart valve 190 is crimped or compressed onto the central region 122 of the flexible member 120, the central region 122 compresses and, because the distal and proximal ends of the flexible member 120 are fixed, the distal region 124 and proximal region 126 of the flexible member 120 expand radially. See FIG. 3. The flexible member 120 may maintain a fluid pathway through the central region 122, as indicated by arrow 128. The radially enlarged distal region 124 and proximal region 126 may prevent axial movement of the heart valve 190 relative to the balloon 170.

Figure 4:
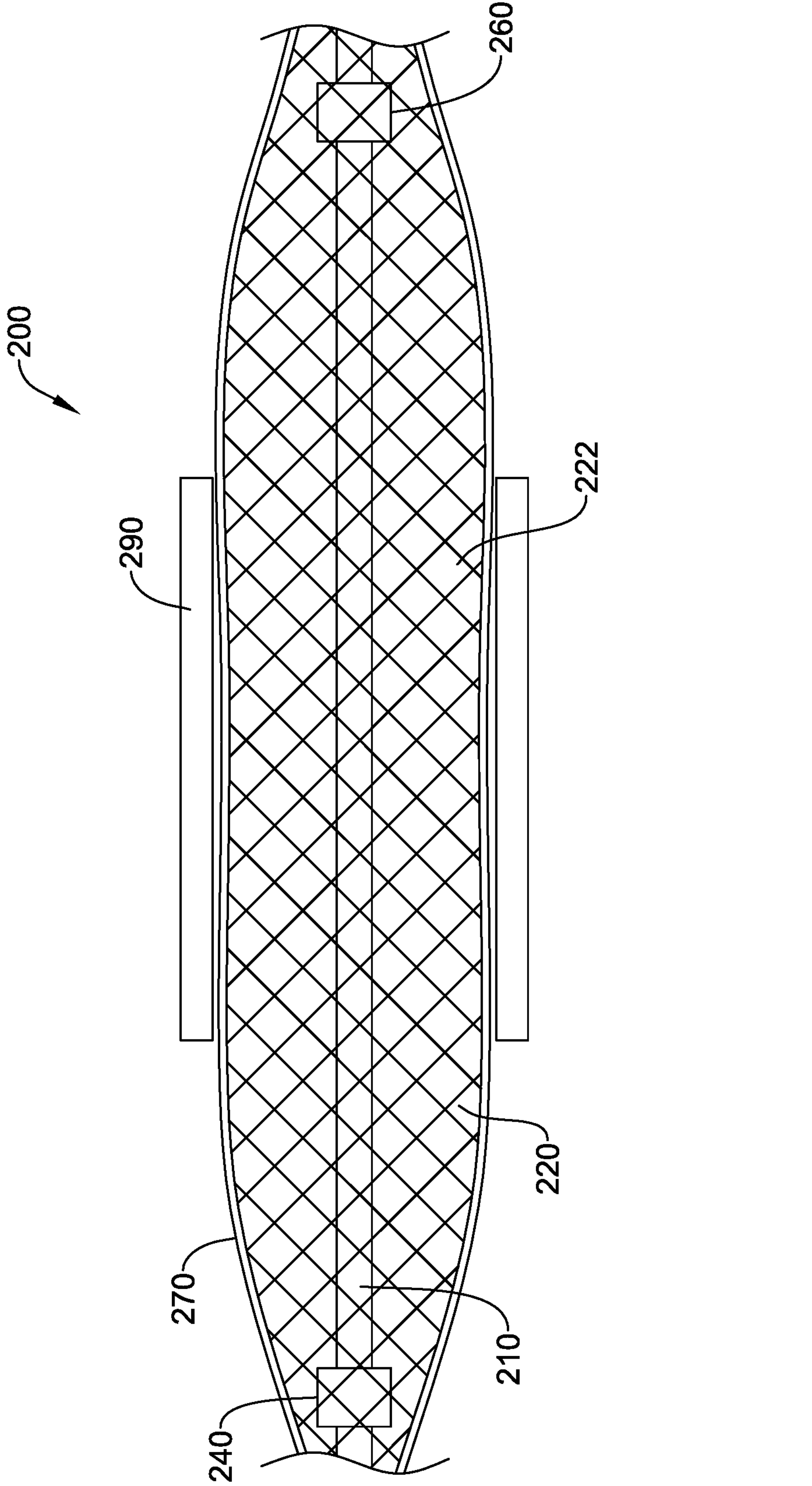
FIG. 4 illustrates another example heart valve delivery system in the relaxed configuration.
Figure 5:
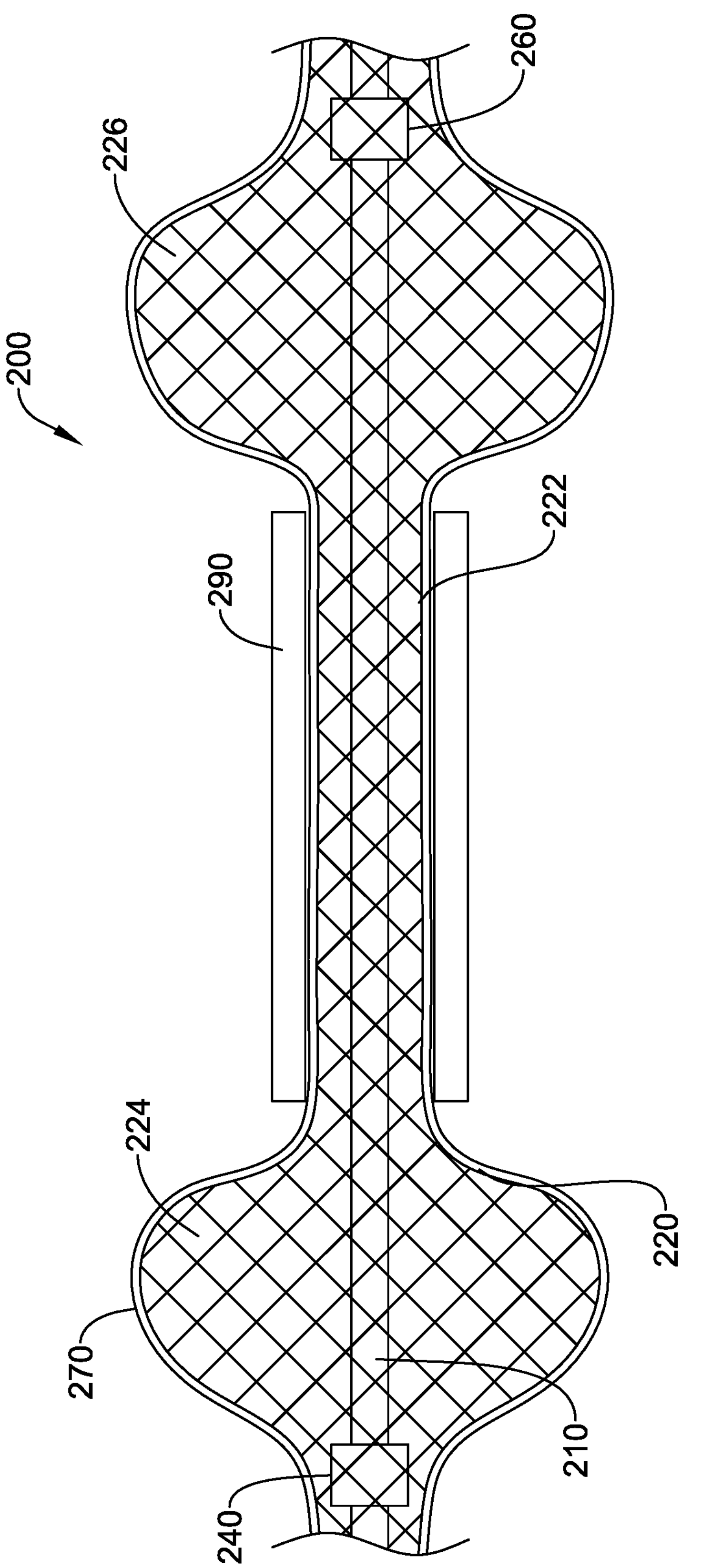
FIG. 5 illustrates the heart valve delivery system of FIG. 4 with the valve crimped onto the central region.

FIG. 4 illustrates another example heart valve delivery system 200, in which the flexible member 220 is a braid disposed over the inner member 210. The braid 220 may be formed from a plurality of filaments that may be fixed to the distal stop 240 and the proximal stop 260. In some examples, the flexible member 220 may also include a textile woven mesh disposed over the braid. For example, the woven mesh may be polytetrafluoroethylene (PTFE). The balloon 270 may extend over the braided flexible member 220 and over the distal stop 240 and proximal stop 260. The valve 290 may be crimped onto the balloon 270 in the central region 222 of the braided flexible member 220. Crimping or compressing the valve 290 may cause the braided flexible member 220 in the central region 222 to be compressed while causing radial expansion of the braided flexible member 220 in the distal region 224 and the proximal region 226, as shown in FIG. 5.

Figure 6:
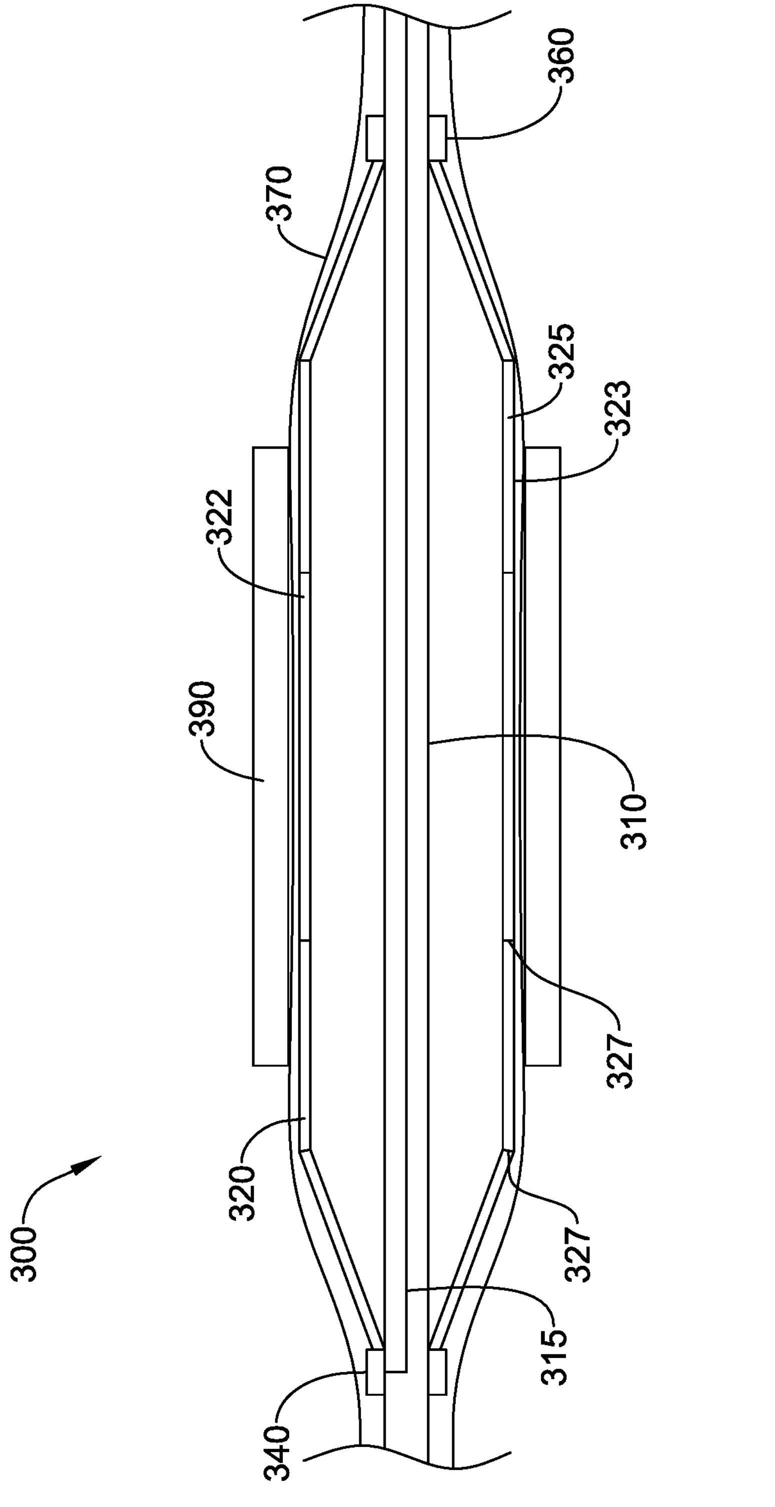
FIG. 6 illustrates a further example heart valve delivery system in the relaxed configuration.
Figure 7:
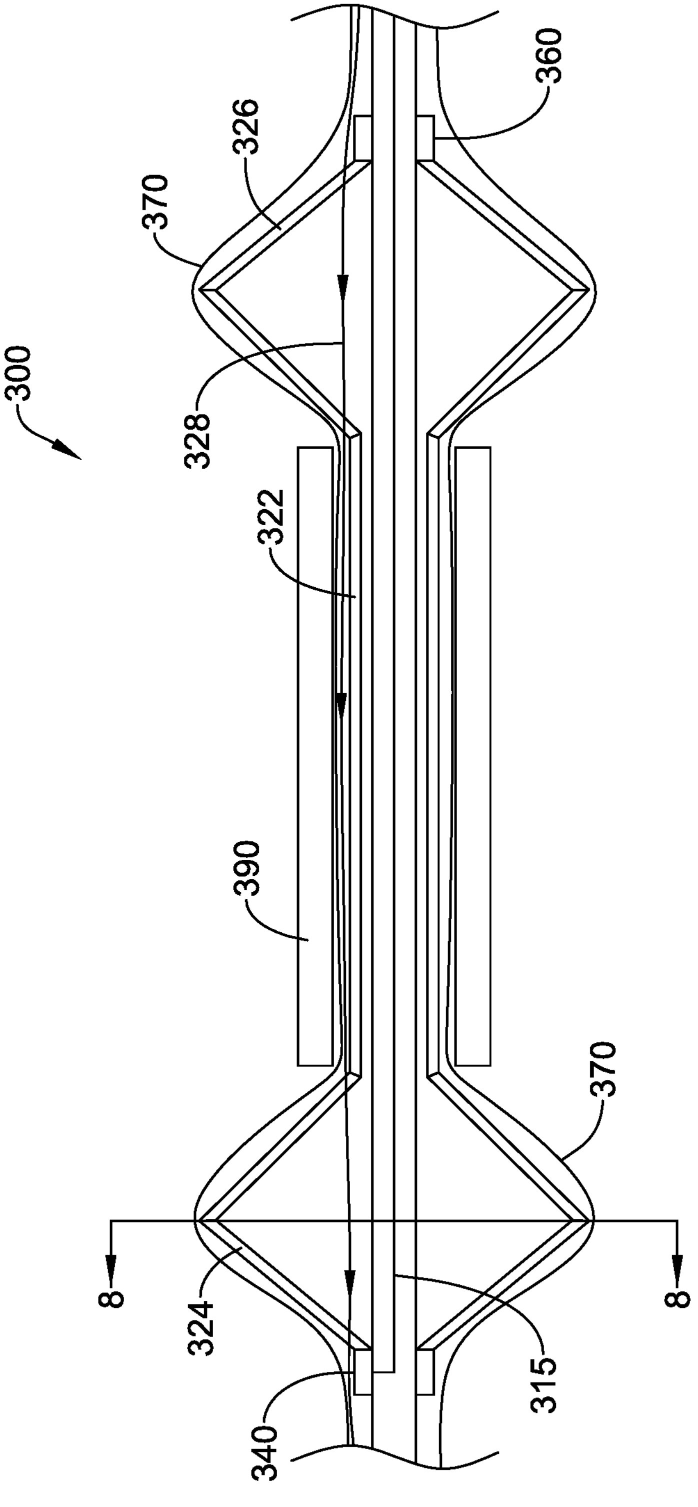
FIG. 7 illustrates the heart valve delivery system of FIG. 6 with a heart valve crimped onto the central region.
Figure 8:
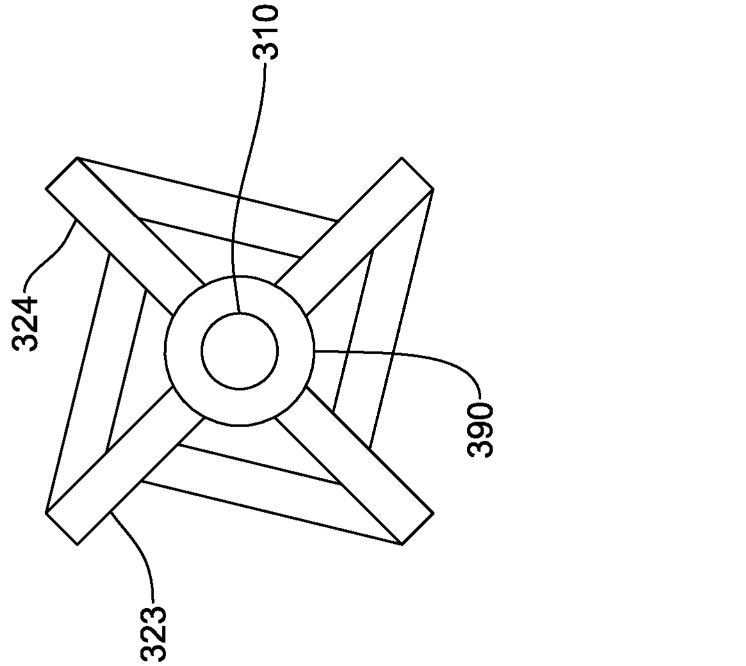
FIG. 8 is a cross-sectional view taken along line 8-8 of FIG. 7.

An additional example heart valve delivery system 300 is illustrated in FIGS. 6-8, in which the flexible member 320 is a frame including a plurality of struts 323 spaced apart circumferentially around the inner member 310. In some examples, the frame may include two, three, four, five, six or more struts 323. In the embodiment shown in FIG. 6, the delivery system 300 includes four struts 323. The figure is a cross-sectional view, thus the top and bottom struts are seen, with the rear strut hidden behind the inner member 310. Each strut 323 may include a plurality of linear regions 325 coupled to one another at bend regions 327. As illustrated, each strut 323 includes five linear regions 325 and six bend regions 327. A balloon 370 may extend over the flexible member 320 and over the distal stop 340 and proximal stop 360. FIG. 6 illustrates the delivery system 300 in the biased relaxed configuration, in which the central region 322 of the flexible member 320 is spaced apart from the elongate inner member 310.

The proximal stop 360 may be fixed to the elongate inner member 310 and the distal stop 340 may be slidable relative to the elongate inner member 310. A pull wire 315 may be fixed to the distal stop 340 and extend proximally through or adjacent the elongate inner member 310. Proximally pulling the pull wire 315 as the valve 390 is compressed or crimped onto the balloon 370 in the central region 322 of the flexible member 320 will move the flexible member 320 from the biased relaxed configuration as shown in FIG. 6, to a compressed configuration in which the central region 322 is adjacent the elongate inner member 310 and the distal and proximal regions of the frame are radially expanded, as shown in FIG. 7. The flexible member 320 may maintain a fluid pathway through the central region 322, as indicated by arrow 328. In other embodiments, no pull wire is present, and the radial compressing force used to crimp or compress the valve 390 may cause the strut linear regions 325 in the central region 322 to be compressed while causing radial expansion of the distal region 324 and the proximal region 326.

FIG. 8 shows the cross-sectional view taken along line 8-8 in FIG. 7. The cross-sectional view illustrates the spaced-apart plurality of struts 323 in the extended position, with the valve 390 compressed over the elongate inner member 310. As shown in FIGS. 7 and 8, the proximal region 326 and the distal region 324 extend radially outward beyond an outer diameter of the crimped heart valve 390, thereby securely holding the valve 390 in place and preventing axial movement of the valve relative to the balloon 370 during delivery.

Figure 9:
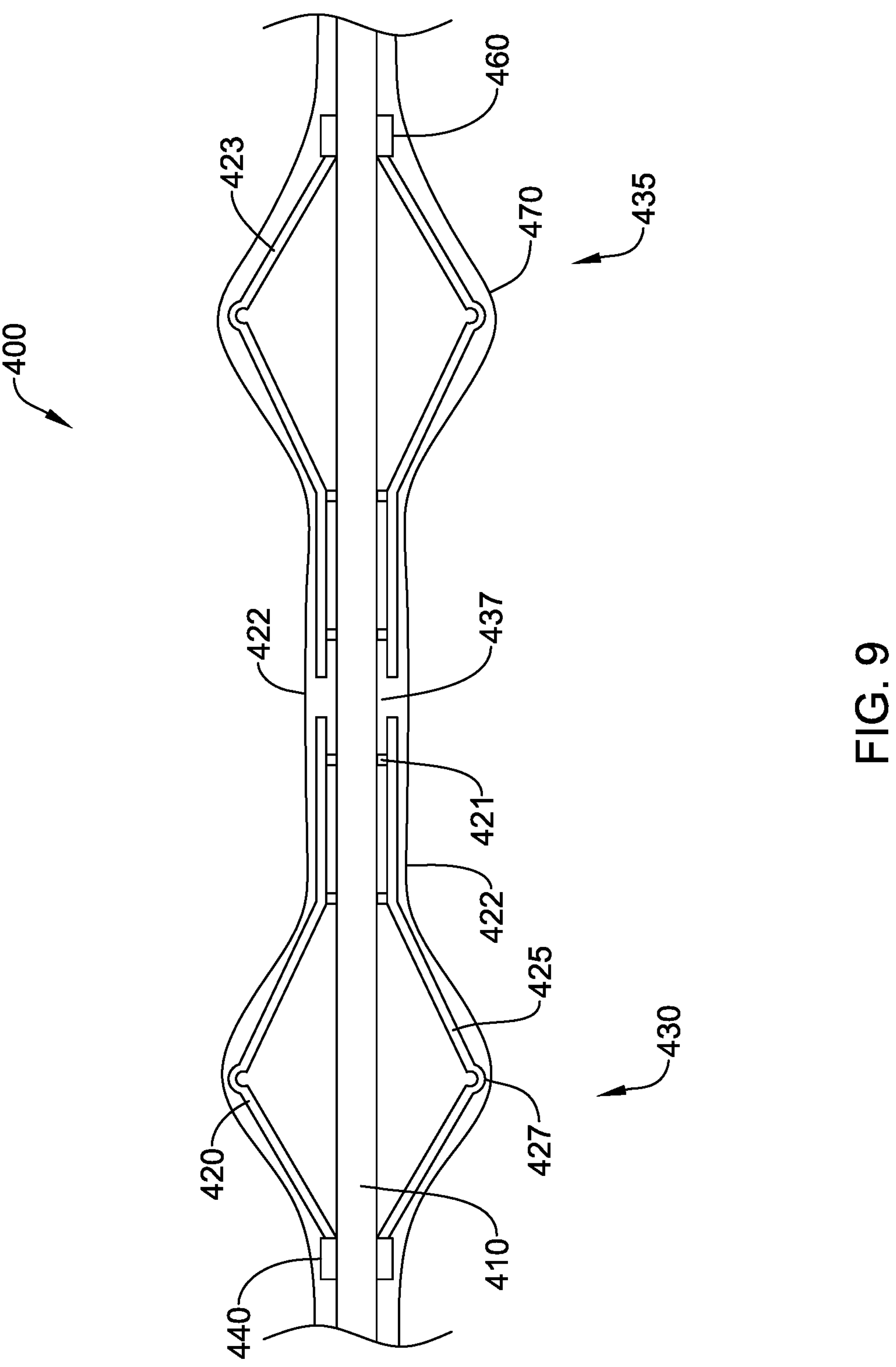
FIG. 9 illustrates an additional example heart valve delivery system in the relaxed configuration.
Figure 10:
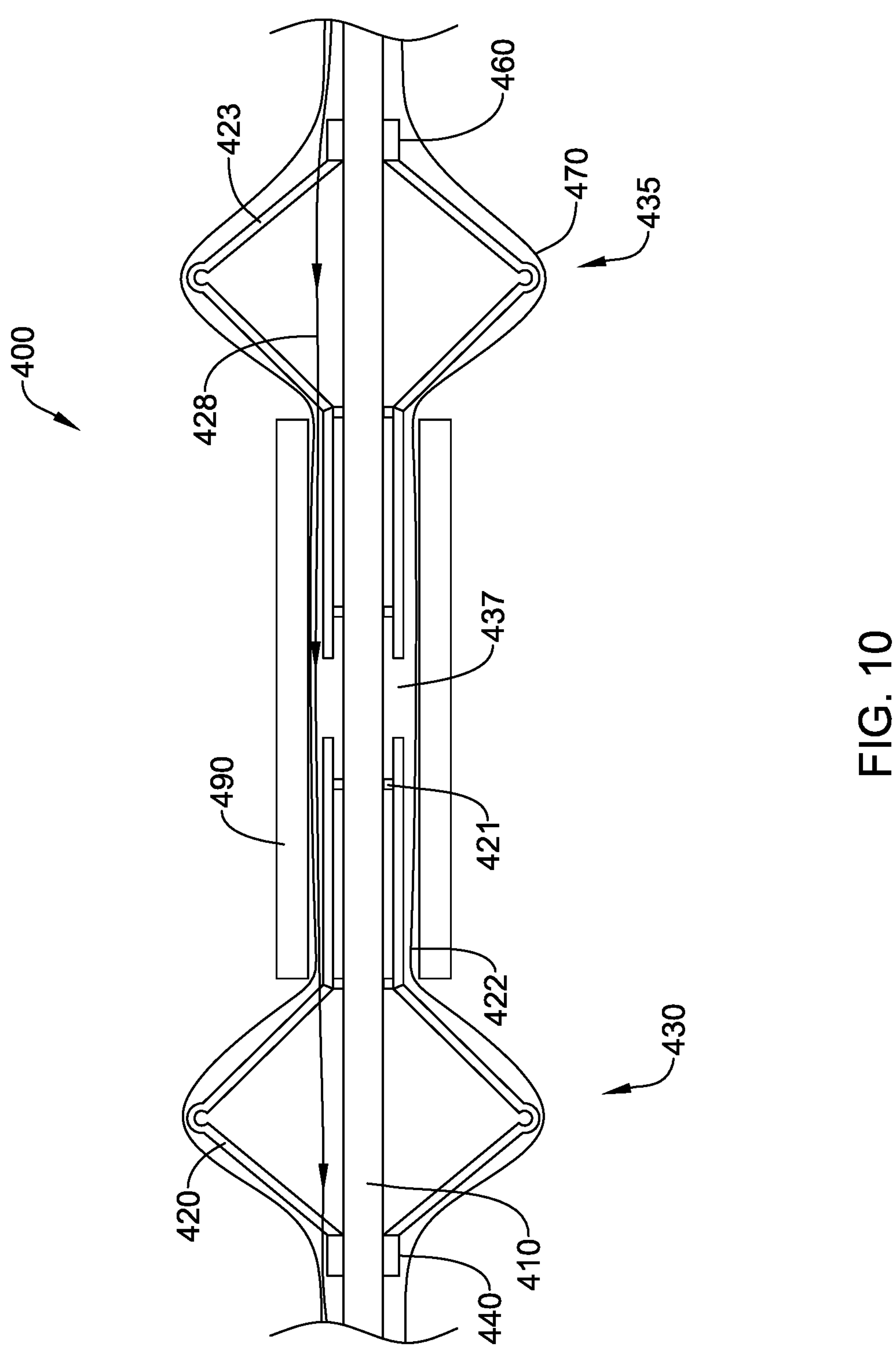
FIG. 10 illustrates the heart valve delivery system of FIG. 9 with a heart valve crimped onto the central region.

FIGS. 9 and 10 illustrate another embodiment of heart valve delivery system 400, in which the flexible member 420 is a frame 420 including a plurality of struts 423 spaced apart circumferentially around the inner member 410. In some examples, the frame may include two, three, four, five, six or more struts 423. In the embodiment shown in FIG. 9, the delivery system 400 includes four struts 423. The figure is a cross-sectional view, thus the top and bottom struts are seen, with the rear strut hidden behind the inner member 410. Each strut 423 may include a plurality of linear regions 425 coupled to one another at bend regions 427. The delivery system 400 differs from the delivery system 300 shown in FIGS. 6 and 7 in that the frame 420 has two portions separated longitudinally by a gap 437. The distal portion 430 of the frame 420 may include the distal stop 440 fixed to the elongate inner member 410 and a plurality of struts 423 spaced apart circumferentially around the inner member 410, fixed to the distal stop 440 and extending proximally therefrom. As illustrated, each strut 423 of the distal portion 430 includes three linear regions 425 and three bend regions 327. The proximal portion 435 of the frame 420 may include the proximal stop 460 fixed to the elongate inner member 410 and a plurality of struts 423 spaced apart circumferentially around the inner member 410 and fixed to the proximal stop 460 and extending distally therefrom. As illustrated, each strut 423 of the proximal portion 435 includes three linear regions 425 and three bend regions 327. A proximal section of the distal portion 430 and a distal section of the proximal portion 435 define a central region 422 configured to receive a heart valve A balloon 470 may extend over the flexible member 420 and over the distal stop 440 and proximal stop 460. FIG. 9 illustrates the delivery system 400 in the biased relaxed configuration, in which the gap 437 between struts 423 of the distal portion 430 and the proximal portion 435 is relatively small and the central region 422 of the frame 420 may be shorter than a valve to be crimped onto the frame 420. In some embodiments, the frame 420 may include protrusions 421 on an inner surface of at least some of the plurality of struts 423. The protrusions 421 may be configured to slide along the elongate inner member 410 as the struts 423 move axially, widening the gap 437.

FIG. 10 shows the delivery system 400 with a valve 490 crimped onto the central region 422. As the valve is crimped, the separate distal portion 430 and proximal portion 435 side axially apart, widening the gap 437 and radially expanding the distal and proximal regions of the frame 420. The flexible member 420 may maintain a fluid pathway through the central region 422, as indicated by arrow 428.

In any of the above embodiments, one or both of the distal and proximal stops may include radiopaque material and function as marker bands.

It will be understood that the dimensions and angles described in association with the above examples are illustrative only, and that other dimensions and angles of the transition zone are contemplated. The materials that can be used for the various components of the steerable catheter (and/or other systems or components disclosed herein) and the various elements thereof disclosed herein may include those commonly associated with medical devices. For simplicity purposes, the following discussion makes reference to the heart valve delivery system 100 (and variations, systems or components disclosed herein). However, this is not intended to limit the devices and methods described herein, as the discussion may be applied to the other heart valve delivery systems 200, 300, 400, and elements, members, components, or devices disclosed herein.

In some embodiments, the heart valve delivery system 100 (and variations, systems or components thereof disclosed herein) may be made from a metal, metal alloy, polymer (some examples of which are disclosed below), a metal-polymer composite, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; cobalt chromium alloys, titanium and its alloys, alumina, metals with diamond-like coatings (DLC) or titanium nitride coatings, other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super-elastic varieties, may exhibit distinct and useful mechanical properties. Linear elastic and/or non-super-elastic nitinol may be distinguished from super-elastic nitinol in that the linear elastic and/or non-super-elastic nitinol does not display a substantial "super-elastic plateau" or "flag region" in its stress/strain curve like super-elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super-elastic plateau and/or flag region that may be seen with super-elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super-elastic nitinol in that linear elastic and/or non-super-elastic nitinol may accept up to about 2-5% strain while remaining substantially elastic (e.g., before plastically deforming) whereas super-elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. For example, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a super-elastic alloy, for example a super-elastic nitinol can be used to achieve desired properties.

In at least some embodiments, portions or all of the heart valve delivery system 100 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the heart valve delivery system 100 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the heart valve delivery system 100 (and variations, systems or components thereof disclosed herein) to achieve the same result.

In some embodiments, the heart valve delivery system 100 (and variations, systems or components thereof disclosed herein) and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex® high-density polyethylene, Marlex® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, Elast-Eon® from AorTech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A delivery system for an expandable prosthetic heart valve, comprising:

an elongate inner member;

a distal stop disposed on the elongate inner member and a proximal stop spaced apart from the distal stop and disposed on the elongate inner member, wherein at least one of the proximal and distal stops is fixed to the elongate inner member;

a flexible member disposed around the elongate inner member, the flexible member having a distal end fixed to the distal stop, a central region, and a proximal end fixed to the proximal stop; and an inflatable balloon disposed over the flexible member;

wherein the flexible member is configured such that when a heart valve is crimped onto the central region, the central region compresses and proximal and distal regions of the flexible member expand radially to prevent axial movement of the heart valve; and wherein the flexible member is biased in a relaxed configuration with the central region spaced apart from the elongate inner member.

2. The delivery system of claim 1, wherein the elongate inner member defines a guidewire lumen.

3. The delivery system of claim 1, wherein when in the relaxed configuration, outer diameters of the central region, proximal region, and distal region are substantially the same.

4. The delivery system of claim 1, wherein the flexible member is a coil.

5. The delivery system of claim 1, wherein the flexible member is a braid.

6. The delivery system of claim 5, further comprising a textile woven mesh disposed over the braid.

7. The delivery system of claim 1, wherein the flexible member is a frame including a plurality of struts spaced apart circumferentially around the elongate inner member, each strut having linear regions and bend regions.

8. The delivery system of claim 7, wherein the proximal stop is fixed to the elongate inner member and the distal stop is slidable relative to the elongate inner member, the delivery system further comprising a pull wire fixed to the distal stop and extending proximally therefrom, wherein proximally pulling the pull wire moves the flexible member from a biased relaxed configuration in which the central region is spaced apart from the elongate inner member, to a compressed configuration in which the central region is adjacent the elongate inner member and the distal and proximal regions of the frame are radially expanded.

9. The delivery system of claim 8, wherein the frame includes protrusions on an inner surface of at least some of the plurality of struts, the protrusions configured to slide along the elongate inner member as the central region of the frame compresses and the proximal and distal regions expand.

10. The delivery system of claim 1, further comprising a prosthetic heart valve crimped onto the central region, wherein the proximal and distal regions of the flexible member extend radially outward beyond an outer diameter of the crimped heart valve.

11. A delivery system for an expandable prosthetic heart valve, comprising:

an elongate inner member defining an inner lumen;

a distal stop fixed to the elongate inner member and a proximal stop fixed to the elongate inner member, the proximal stop spaced apart from the distal stop;

a flexible member disposed around the elongate inner member, the flexible member having a distal end fixed to the distal stop, a central region, and a proximal end fixed to the proximal stop, the flexible member biased in a relaxed configuration with the central region spaced apart from the elongate inner member; and an inflatable balloon disposed over the flexible member;

wherein the flexible member is configured such that when a heart valve is crimped onto the central region, the central region moves from the relaxed configuration to a compressed configuration in which the central region is adjacent the elongate inner member and proximal and distal regions of the flexible member expand radially to prevent axial movement of the heart valve.

12. The delivery system of claim 11, wherein when in the relaxed configuration, outer diameters of the central region, proximal region, and distal region are substantially the same.

13. The delivery system of claim 11, wherein the flexible member is a coil.

14. The delivery system of claim 11, wherein the flexible member is a braid.

15. The delivery system of claim 14, further comprising a textile woven mesh disposed over the braid.

16. The delivery system of claim 11, further comprising a prosthetic heart valve crimped onto the central region, wherein the proximal and distal regions of the flexible member extend radially outward beyond an outer diameter of the crimped heart valve.

17. A delivery system for an expandable prosthetic heart valve, comprising:

an elongate inner member;

a distal stop fixed to the elongate inner member and a proximal stop spaced apart from the distal stop and fixed to the elongate inner member;

a flexible member disposed around the elongate inner member, the flexible member having a distal portion fixed to the distal stop, and a separate proximal portion fixed to the proximal stop, wherein the distal portion and the proximal portion are spaced apart longitudinally, wherein a proximal section of the distal portion and a distal section of the proximal portion define a central region configured to receive a heart valve; and an inflatable balloon disposed over the flexible member;

wherein the flexible member is configured such that when the heart valve is crimped onto the central region, the proximal portion of the flexible member moves proximally into a radially expanded configuration, and the distal portion of the flexible member moves distally into a radially expanded configuration, thereby preventing axial movement of the heart valve; and wherein the flexible member is biased in a relaxed configuration with the central region spaced apart from the elongate inner member.

18. The delivery system of claim 17, wherein the distal portion and the proximal portion of the flexible member are frames including a plurality of struts spaced apart circumferentially around the elongate inner member, each strut having linear regions and bend regions.

19. The delivery system of claim 18, further comprising a plurality of protrusions disposed on an inner surface of at least some of the plurality of struts, wherein the plurality of protrusions are configured to slide along the elongate inner member as the plurality of struts move axially when the distal and proximal portions of the flexible member move into the radially expanded configuration.

* * * * *